United States Patent [19]

Sakata et al.

[11] Patent Number: 4,695,539

[45] Date of Patent: * Sep. 22, 1987

[54] PROCESS FOR QUANTITATIVE DETERMINATION OF SUBSTRATE TREATED WITH OXIDASE

[75] Inventors: Yoshitsugu Sakata, Otsu; Yoshibonu Miyashita, Osaka; Tadashi Hamanaka, Kobe; Hiroyuki Kodera; Yutaka Miki, both of Amagasaki; Kazuhiko Yamanishi, Tokyo; Toshiro Hanada, Kawagoe, all of Japan

[73] Assignee: Wako Pure Chemical Industries, Ltd., Osaka, Japan

[ * ] Notice: The portion of the term of this patent subsequent to Sep. 22, 2004 has been disclaimed.

[21] Appl. No.: 516,241

[22] Filed: Jul. 22, 1983

[30] Foreign Application Priority Data

Sep. 29, 1982 [JP] Japan ................................ 57-170639

[51] Int. Cl.$^4$ .................... C12Q 1/62; C12Q 1/60; C12Q 1/54; C12Q 1/26; C12Q 1/28
[52] U.S. Cl. ........................................ 435/10; 435/11; 435/14; 435/25; 435/28; 435/810
[58] Field of Search ....................... 435/10, 11, 14, 25, 435/28, 817, 810

[56] References Cited

U.S. PATENT DOCUMENTS 4,353,983 10/1982 Siddiqi ................................ 435/14

FOREIGN PATENT DOCUMENTS 0054358 6/1982 European Pat. Off. ............ 435/28

4058490 5/1979 Japan ................................ 435/25

OTHER PUBLICATIONS

Stryer L. (1975), Biochemistry, 2d ed., p. 344.
Porras et al. (1981), The Reaction of Reduced Xanthine Oxidase with Oxygen, J. Biol. Chem., 256(17): 9096–9103.
Matkovics et al. (1975), Utilization of Catalase and Superoxide Dismutase to Clarify the Mechanism of Action of Oxidases, Proc. Hung Annu. Meet. Biochem., 15: 95, Chem. Abstr. 88: 46907w.
Galliana et al. (1980), Formation of Superoxide Radical.
Galliani et al. (1980), J. Chem. Soc. Perkins Trans II, 1:1–3.
Halliwell et al. (1982), Interaction of the Superoxide Radical with Peroxidase and with Other Iron Complexes, Oxidase Relat. Redox System Proc. Int. Symp., 3rd, 1979.

Primary Examiner—Esther M. Kepplinger
Attorney, Agent, or Firm—Armstrong, Nikaido, Marmelstein & Kubovcik

[57] ABSTRACT

A substrate in a sample can be determined quantitatively by measuring colorimetrically superoxide ion generated by treating the sample with a specific oxidase corresponding to the substrate to be determined, said oxidase treatment and measuring of the generated superoxide ion being conducted by using a reagent composition comprising (a) an oxidase, (b) peroxidase, (c) a phenol and/or an amine, (d) a thiol compound, (e) a color producing reagent to be reduced, and if necessary (f) a chelating agent.

9 Claims, No Drawings

PROCESS FOR QUANTITATIVE DETERMINATION OF SUBSTRATE TREATED WITH OXIDASE

This invention relates to a process for quantitatively determining a substrate. More particularly, this invention relates to a process for quantitatively determining a substrate such as blood components applying an enzymic reaction in clinical chemical examinations and the like.

In quantitative determination of substrates by means of enzymes, particularly oxidases, the products by the enzymic reactions are water, carbon dioxide gas and hydrogen peroxide. Recently, the measurement of the produced hydrogen peroxide for quantitative determination of substrates has gained wide applications due to biochemical knowledge that enzymes have inherent specificity, that is, quantitativeness. As a result, chemical quantitative determinations previously used are hardly employed, since various devices are necessary for maintaining quantitativeness, corrosion of chemicals causes fatal problems, there are some problems in specificity, and the like. But recent enzymic processes are not always sufficiently satisfactory. This can be explained referring to quantitative determination of cholesterol as follows.

An increase of cholesterol causes hypercholesterolemia which is found in nephrosis syndrome, serious diabetes mellitus, dysthyroidism, glycogen accumulation disease, familial hyperlipemia, and the like. On the other hand, a decrease of cholesterol causes hypercholesterinemia which is found in serious liver disease, insufficient nutrition, hyperthyroidism, and the like. The quantitative determination of cholesterol is an essential test item in the field of clinical chemical examinations. As processes for quantitatively determining cholesterol, there were employed Zak-Henry's method and Zurkowsky method wherein the Liebermann-Burchard reaction and the Kiliani reaction were applied to a colorimetric reaction. But, after the proposal of a combination of an enzyme which oxidizes cholesterol to $\Delta^4$-cholestenon and hydrogen peroxide with a reagent for measuring the produced hydrogen peroxide, this enzymic process becomes a major process for quantitative determination of cholesterol. But this enzymic process still requires further improvements, since influences of reducing substances in body fluid cannot be prevented. Further, the sensitivity is insufficient and the use of oxidizable color producing reagents which can produce color at higher wavelength sides is required for improvement.

The present inventors had questions on previous knowledge that enzymic reactions caused by individual specific oxidases for various substrates simply produce final products such as water and hydrogen peroxide and studied enzymic reactions extensively with a hope that new applications can be obtained by studying enzymic reactions. After studies of various combinations of substrates in body fluid and oxidases showing specificity, it was found that superoxide ions were produced quantitatively by enzymic reactions of individual specific oxidases with substrates and said superoxide ions were changed to certain substances such as hydrogen peroxide and that the measurement of superoxide ion made it possible to determine quantitatively the substrates, and accomplished this invention.

This invention provides a process for quantitatively determining a substrate, which comprises treating a substrate with an oxidase and measuring the generated superoxide ion.

The superoxide ion can produce color by reducing a reagent to be reduced. To measure the degree of coloring or the degree of color change is very easy considering today's spectroscopic technique. It is one advantage of this invention to remove influences of bilirubin, ascorbic acid, etc., having slight reducing power present in body fluid by properly selecting a color producing reagent to be reduced. Further, it is another advantage of this invention to select freely a color producing reagent to be reduced which has high sensitivity and can produce color at longer wavelength side.

The superoxide ion changes to hydrogen peroxide, although there may be a difference in speed, and it has been believed that said change can be accelerated by superoxide dismutase usually present in serum (the amount in the serum is very minute, unless hemolysis takes place). Another important thing in this invention is that the course to hydrogen peroxide previously taken is replaced completely by the course to reduction by superoxide. This can be done by the use of a compound having a SH group, that is a thiol compound. The objected effect of thiol compound can be helped and accelerated by the addition of a phenol (including a naphthol, hereinafter the term "phenol" includes naphthols). It is also admitted that the co-use of a peroxidase makes the quantitativeness of the process of this invention sufficiently satisfactory.

According to this invention, a substrate to be measured is treated with an oxidase (a) which has a specificity to said substrate, and the generated superoxide ion quantitatively from the enzymic reaction is measured by applying its reducing properties to quantitatively determine the substrate. In such a case, (b) a peroxidase, (c) an amine and/or a phenol, (d) a thiol compound having a SH group and (e) a color producing reagent to be reduced are used for improving the measuring time, sensitivity, quantitativeness and the like, which properties are necessary for practical application of this invention.

Further, in order to remove autooxidation which is an undesirable side reaction at the time of measurement and probably caused by the thiol compound and the like additives, the addition of a chelating agent is preferable in order to proceed the desired reaction stably. That is, a reagent composition comprising (a) an oxidase, (b) a peroxidase, (c) an amine and/or a phenol, (d) a thiol compound, (e) a color producing reagent to be reduced and (f) a chelating agent is used for such a purpose.

For example, to 0.1 mole of tris buffer (precisely tris-HCl buffer) solution (pH 8.0), there are dissolved $2.5 \times 10^{-5}$ mole of cytochrome C, 15 units/dl of cholesterol oxidase, 600 units/dl of peroxidase, and 0.1% by weight of phenol. To the resulting solution, a solution obtained by dissolving 0.8% by weight of glutathione (reduced form) in the same buffer solution as mentioned above is added. To the resulting mixture, isopropanol containing 200 mg/dl of cholesterol is added and incubated at 37° C. for, e.g. 10 minutes. Cytochrome C forms color and absorbance at a wavelength of 550 nm using the reagent blank as control (i.e., O.D. ($-$B1)) is measured to give 0.10. When only isopropanol is used in place of the isopropanol solution containing cholesterol, there is no color formation of cytochrome C. Further, the same results are obtained when 2,2'-di(4-nitrophenyl)-5,5'-diphenyl-3,3'-(3,3'-dimethoxy-4,4'-diphenylene)ditetrazolium chloride (hereinafter referred to as "NO$_2$-TB") is used as color producing reagent to be reduced. These color formations are found to be damaged by the presence of a large amount of superoxide dismutase which functions specifically to superoxide ion. That is, the color formation used in this invention is admitted to be caused by the reducing action of superoxide ion.

Oxidases are oxidizing enzymes and there are specific oxidases corresponding to individual substrates. Substrates and corresponding specific oxidases usable in this invention can be listed as follows:

| Glucose | Glucose oxidase |
|---|---|
| Cholesterol | Cholesterol oxidase |
| Glycerol | Glycerol oxidase |
| Glycerolphosphate | Glycerolphosphate oxidase |
| Choline | Choline oxidase |
| Acyl CoA | Acyl CoA oxidase |
| Pyruvic acid | Pyruvate oxidase |
| Uric acid | Uricase |
| Xanthine | Xanthine oxidase |
| Lactic acid | Lactate oxidase |

These oxidases can be obtained from living bodies producing these oxidases and can be available commercially as well as peroxidases.

As the amine, there can be used conventional organic amines. Aromatic amines are more effective than aliphatic amines with a small using amount. There can be used primary amines, secondary amines and tertiary amines. Examples of these amines are aniline, N-ethylaniline, N,N-dimethylaniline, N,N-diethylaniline, N,N-diethyl-m-toluidine, N-ethyl-N-β-hydroxyethyl-m-toluidine, and the like. The amine can be used in an amount of 0.0001% to 0.2% by weight in the reaction solution at the stage of color formation.

The phenol is not particularly influenced by other substituents. As the phenol, there can be used phenol, chlorophenol, dichlorophenols, naphthols, sulfonic acid derivatives and the like. The phenol can be used in an amount of 0.0001% to 0.2% by weight in the reaction solution at the stage of color formation.

A phenol and an amine can be used together. Further, there can be used a compound which belongs to phenols and also to amines, for example, 1-N,N-dimethylamino-4-naphthol, 4-N,N-diethylamino salicylic acid, or the like. But in the case of an amine, L-amino acid, or the like substrate and amine oxidase, L-amino acid oxidase, or the like oxidase, the use of phenol, not amine, is, needless to say, preferable.

As the thiol compound, there can be used reduced glutathione, thioglycolic acid mercaptoethanol, thiosalicylic acid, cysteamine, cysteine, dimercaptosuccinic acid, etc. The thiol compound can be used in an amount of 1 to 50 mg/dl in the reaction solution at the stage of color formation.

The color producing reagent to be reduced means a reagent which has a suitable oxidation reduction potential and produces color by the reduction with superoxide ion. Examples of the color producing reagent to be reduced are tetrazolium salts such as NO$_2$-TB, 2-(4-iodophenyl)-3-(4-nitrophenyl)-5-phenyltetrazolium chloride (hereinafter referred to as "INT"). 3-(4,5-dimethylthiazolyl-2)-2,5-diphenyltetrazolium bromide (hereinafter referred to as "MTT"), etc.; cytochrome C, tetranitromethane (very dangerous), plastocyanin, Blue protein, etc.

The color producing reagent to be reduced can be used in an amount of 1 to 40 mg/dl in the reaction solution at the stage of color formation. The tetrazolium compounds had various problems in that formazans produced by reduction of tetrazolium compounds are difficulty soluble in water, quantitativeness of color formation is not good, and devices are contaminated, and the like, but recent development obtained by introducing a group which improves the solubility into tetrazolium compounds solved such problems and makes it possible to employ these compounds in this invention.

As the chelating agent, there can be used ethylenediaminetetraacetic acid (EDTA), trans-cyclohexanediaminetetraacetic acid or trans-1,2-cyclohexanediamine-N,N,N',N'-tetraacetic acid (CyDTA), diethylenetetraminepentaacetic acid or diethylenetriamine-N,N,N',N'-pentaacetic acid (DTPA), etc. The chelating agent can be used in an amount of 0.5 to 5 millimol/dl in the reaction solution at the stage of color formation. The addition of the chelating agent makes the variation of reagent blank values small.

The peroxidase can be used in an amount of 50 to 1000 units/dl in the reaction solution at the state of color formation.

In the case of using the above-mentioned compounds in proper combination, if the final mixture to be measured on its coloring is clouded so as to damage the measurement, a surface active agent or solubility aid can be added thereto according to a conventional process.

The presence of anticoagulants such as heparin, sodium citrate, sodium oxalate, etc., and glycolytic inhibitors such as sodium fluoride, etc., do not influence the color formation according to the process and reagents of this invention. Further, the presence of ascorbic acid, bilirubin, hemoglobin, uric acid, pyruvic acid, glucose and the like which are present in a living body physiologically, or pathologically, or by the dosage for treatment, do not influence the color formation according to the process and reagents of this invention because of specificity of individual oxidases for objected substrates.

In practical measurement, to a sample to be tested, a mixture of (a) a special oxidase for a substrate to be determined, (b) peroxidase, (c) an amine and/or a phenol, (d) a thiol compound, and (e) a color producing reagent to be reduced, and if necessary for better results, (f) a chelating agent is added in a suitable medium (usually in a buffer solution) and incubated so as to proceed the desired reaction to a desired degree, and the resulting color formation or color change is measured to quantitatively determine the substrate content in the sample. For such a purpose, the oxidase and the like additives and reagents are mixed into one or into several groups or can be used alone. Various combinations of the above-mentioned additives and reagents, alone or as a mixture thereof, are possible for providing the reagents used in the process of this invention. The medium for the reagents or the reaction solution is preferably made pH 7.0 or more, more preferably 7.5 or more, during the determination.

As mentioned above, this invention provides a process and a mixture of reagents for quantitative determination of a substrate in body fluid component wherein superoxide ion is measured. Such an invention is epoch-making and contributes to this field of art greatly.

This invention is illustrated by way of the following Examples.

EXAMPLE 1

(Cholesterol)

A color producing reagent solution is prepared by dissolving in 0.1M tris buffer solution (pH 8.0) 20 mg/dl of $NO_2$-TB, a phenol or amine compound as listed in Table 1 in an amount of 1.06 mM/l, 0.65 mM/l. of reduced glutathione, 300 U/dl of peroxidase, 15 U/dl of cholesterol oxidase, 0.1 g/dl of Triton X-100 (octyl-phenoxypolyethoxyethanol—available from Rohm and Haas Co.) and 0.4 g/dl of Emalgen 920 (available from Kao-Atlas Co., Ltd.). On the other hand, a sample solution to be tested is prepared by dissolving 200 mg of cholesterol in isopropanol and making the volume 100 ml.

To 50 μl of the sample solution, 3.0 ml of the color producing solution is added and incubated at 37° C. for 10 minutes. Absorbance at wavelength of 560 nm is measured using each reagent blank as control.

The results are as shown in Table 1. As is clear from Table 1, the effect of addition of phenols or amines is remarkable.

TABLE 1

| Amine or Phenol | O.D. (-Bl) |
| --- | --- |
| No addition | 0.39 |
| Phenol | 1.27 |
| p-Chlorophenol | 1.24 |
| o-Chlorophenol | 1.25 |
| m-Chlorophenol | 1.23 |
| 2,4,6-Trichlorophenol | 1.24 |
| Aniline | 1.26 |
| N—Ethylaniline | 1.27 |
| N,N—Diethylaniline | 1.26 |
| N,N—Dimethyl-m-toluidine | 1.26 |
| N—Ethyl-N—β-hydroxyethyl-m-toluidine | 1.27 |
| 4-Diethylaminosalicylic acid | 1.15 |
| 1-Dimethylaminonaphthalene-7-sulfonic acid | 1.22 |
| 1-Naphthol-8-sulfonic acid | 1.04 |

EXAMPLE 2

(cholesterol)

A color producing reagent solution is prepared by dissolving in 0.1M tris buffer solution (pH 8.0) 20 mg/dl of $NO_2$-TB, 1.06 mM/l. of phenol, 0.65 mM/l. of a thiol compound as listed in Table 2, 300 U/dl of peroxidase, and 15 U/dl of cholesterol oxidase. On the other hand, a sample solution to be tested is prepared by dissolving 200 mg of cholesterol in isopropanol and making the volume 100 ml.

To 50 μl of the sample solution, 3.0 ml of the color producing reagent solution is added and measured in the same manner as described in Example 1. The results are shown in Table 2. As is clear from Table 2, the effect of addition of thiol compound is remarkable.

TABLE 2

| Thiol compound | O.D. (-Bl) |
| --- | --- |
| No addition | 0.03 |
| Glutathione (reduced form) | 1.27 |
| Thioglycolic acid | 1.26 |
| L-Cysteine | 2.24 |
| Cysteamine | 1.57 |
| Thiosalicylic acid | 1.25 |
| Dimercaptosuccinic acid | 1.03 |

EXAMPLE 3

(Cholesterol)

A first color producing reagent solution is prepared by dissolving in 0.1M tris buffer solution (pH 8.0) 10 mg/dl of $NO_2$-TB, 0.1% by weight of phenol, 0.13% by weight of Triton X-100, 600 U/dl of peroxidase (Biozyme Co.), 15 U/dl of cholesterol oxidase (available from Amano Pharmaceutical Co., Ltd. 2.16 U/mg), and 100 U/dl of cholesterol esterase (available from Amano Pharmaceutical Co., Ltd., 29.2 U/mg). A second color producing reagent solution is prepared by dissolving in 0.1M tris buffer solution (pH 8.0) 800 mg/dl of glutathione (reduced form).

Sample A is distilled water as blank, Sample B is an isopropanol solution containing 200 mg/dl of cholesterol and Sample C is human blood serum containing 289 mg/dl of cholesterol, said value being obtained by a conventional measuring method.

The first and second color producing reagent solutions are incubated at 37° C. Three mixed solutions are prepared by mixing 4 ml of the first color producing reagent solution with 100 μl of the second color producing reagent solution. After 15 seconds, each 20 μl of Samples A, B and C is added to each resulting mixture and incubated at 37° C. for 10 minutes. By measuring the absorbance at 560 nm ($O.D._{560}$), the content in Sample C is calculated as 285 mg/dl using the results shown in Table 3.

TABLE 3

| | $O.D._{560}$ | | O.D. (-Bl) | |
| --- | --- | --- | --- | --- |
| Sample A | Sample B | Sample C | B − A | C − A |
| 0.103 | 0.497 | 0.665 | 0.394 | 0.562 |

When 18 samples, the cholesterol content of which are determined as 155 to 285 mg/dl according to a conventional method, are quantitatively determined using the reagents of Example 3, there are obtained the correlation coefficient of 0.923 and regression line
$Y = 1.002 \times -14.5$.

When 2.5 mMol/l. of EDTA is added to the first color producing reagent solution and the second color producing reagent solution is added to the resulting mixture, the change of reagent blank value Δ is is 0.002/min. On the other hand, when no EDTA is added, the change of reagent blank Δ is 0.010/min.

EXAMPLE 4

(Acyl CoA)

A color producing reagent solution is prepared by dissolving in 0.1M tris buffer solution (pH 8.0) 10 mg/dl of $NO_2$-TB, 0.1% by weight of phenol, 600 U/dl of peroxidase (derived from horseradish, available from Biozyme Co.), 20 mg/dl of glutathione (reduced form), and 240 U/dl of acyl CoA oxidase (available from Toyo Jozo Kabushiki Kaisha).

Sample A is distilled water as blank, and Sample B is a 2 mM aqueous solution of palmitoyl CoA (available from Toyo Jozo Kabushiki Kaisha, content 93.6%).

Each 3 ml of the color producing reagent solution is placed in two test tubes and each 100 μl of Sample A or B is added and incubated at 37° C. for 10 minutes. Absorbance of Sample B is measured at wavelength of 560 nm using Sample A as control. Sample B is diluted with distilled water 2 and 4 times to give Samples B′ and B″, which are measured in the same manner as described above. The results are as shown in Table 4. As is clear from Table 4, there is obtained a linear calibration curve.

TABLE 4

| Sample | B | B' | B'' |
| --- | --- | --- | --- |
| O.D. (-Bl) | 0.994 | 0.500 | 0.247 |

EXAMPLE 5

(Glucose)

A color producing reagent solution is prepared by dissolving in 0.1M phosphate buffer solution (pH 8.0) 10 mg/dl of INT, 0.1% by weight of 3,5-dimethoxy-N-ethyl-N-(2-hydroxy-3-sodium sulfopropyl)aniline, 600 U/dl of peroxidase (available from Biozyme Co.), 20 mg/dl of glutathione (reduced form), and 3000 U/dl of glucose oxidase (available from Amano Pharmaceutical Co., Ltd.).

Sample A is distilled water as blank, Sample B is an aqueous solution containing 200 mg/dl of glucose, and Sample C is human blood serum containing 121 mg/dl of glucose, said value being obtained by a conventional measuring method. Further, Sample C is diluted with distilled water 2 and 4 times to give Samples C' and C'', respectively.

Each 3 ml of the color producing reagent solution is placed in 5 test tubes and each 20 μl of Samples A, B, C, C' and C'' is added to each test tube, followed by incubation at 37° C. for 10 minutes. Immediately, absorbances of Samples B to C'' are measured at wavelength of 500 nm using Sample A as control. The results are shown in Table 5.

TABLE 5

| Sample | A | B | C | C' | C'' |
| --- | --- | --- | --- | --- | --- |
| O.D.$_{560}$ | 0.104 | 1.104 | 0.705 | 0.410 | 0.250 |
| O.D. (-Bl) | — | 1.000 | 0.601 | 0.306 | 0.146 |

From the above results, the content of glucose in Sample C is calculated as 120 mg/dl. There is admitted linearity of the calibration curve from the data of Samples C, C' and C''.

EXAMPLE 6

(Pyruvic acid)

A color producing reagent solution is prepared by dissolving in 0.02M phosphate buffer solution (pH 7.1) 20 mg/dl of NO$_2$-TB, 0.1% by weight of phenol, 600 U/dl of peroxidase (available from Biozyme Co.), 10 mg/dl of glutathione (reduced form), 700 U/dl of pyruvate oxidase (available from Toyo Jozo Kabushiki Kaisha), 2 mg/dl of flavin adenine dinucleotide, 44 mg/dl of thiamine pyrophosphate, and 0.15% by weight of magnesium acetate.

Sample A is distilled water as blank, and Sample B is an aqueous solution containing lithium pyruvate in an amount of 10 mg/dl as pyruvic acid.

Each 3 ml of the color producing reagent solution is placed in two test tubes and each 100 μl of Samples A and B is added to each test tube and incubated at 37° C. for 15 minutes. Immediately, absorption at wavelength of 560 nm of Sample B is measured using Sample A as control to give the value of 0.042.

EXAMPLE 7

(Choline)

A color producing reagent solution is prepared by dissolving in 0.1M tris buffer solution (pH 8.0) 10 mg/dl of NO$_2$-TB, 0.1% by weight of phenol, 600 U/dl of peroxidase (available from Biozyme Co.), 10 mg/dl of thiosalicylic acid, and 500 U/dl of choline oxidase (available from Toyo Jozo Kabushiki Kaisha).

Sample A is distilled water as blank, and Sample B is an aqueous solution containing 70 mg/dl of choline chloride. Sample B is diluted with distilled water 2 and 4 times to give Samples B' and B'', respectively.

Each 3 ml of the color producing reagent solution is placed in 4 test tubes and each 20 μl of Samples A, B, B' and B'' is added to each test tube, followed by incubation at 37° C. for 10 minutes. Immediately, absorbances of Samples B to B'' are measured at wavelength of 560 nm using Sample A as control. The results are shown in Table 6.

TABLE 6

| Sample | B | B' | B'' |
| --- | --- | --- | --- |
| O.D. (-Bl) | 1.100 | 0.581 | 0.281 |

EXAMPLE 8

(Glycerol-3-phosphate)

A color producing reagent solution is prepared by dissolving in 0.1M tris buffer solution (pH 8.0) 10 mg/dl of NO$_2$-TB, 0.05% by weight of phenol, 600 U/dl of peroxidase (available from Biozyme Co.), 20 mg/dl of glutathione (reduced form), and 600 U/dl of glycerol-3-phosphate oxidase (available from Toyo Jozo Kabushiki Kaisha).

Sample A is distilled water as blank and Sample B is an aqueous solution containing 10 mM (172 mg/dl) of glycerol-3-phosphate. Sample B is diluted with distilled water 2 and 4 times to give Samples B' and B'', respectively.

Each 4 ml of the color producing reagent solution is placed in 4 test tubes and each 50 μl of Samples A, B, B' and B'' is added to each test tube, followed by incubation at 37° C. for 10 minutes. Immediately, absorbances of Samples B to B'' are measured at wavelength of 560 nm using Sample A as control. The results are shown in Table 7.

TABLE 7

| Sample | B | B' | B'' |
| --- | --- | --- | --- |
| O.D. (-Bl) | 0.678 | 0.344 | 0.169 |

EXAMPLE 9

(Glycerol)

A color producing reagent solution is prepared by dissolving in 0.05M phosphate buffer solution 10 mg/dl of NO$_2$-TB, 0.05% by weight of phenol, 600 U/dl of peroxidase (available from Biozyme Co.), 20 mg/dl of glutathione (reduced form), and 600 U/dl of glycerol oxidase (available from Kyowa Hakko Kogyo Co., Ltd.)

Sample A is distilled water as blank, and Sample B is an aqueous solution containing 2 mM of glycerin. Sample B is diluted with distilled water 2 and 4 times to give Samples B' and B'', respectively.

Each 4 ml of the color producing reagent solution is placed in 4 test tubes and each 50 μl of Samples A, B, B' and B" is added to each test tube, followed by incubation at 37° C. for 10 minutes. Immediately, absorbances of Samples B to B" are measured at wavelength of 560 nm using Sample A as control. The results are shown in Table 8.

TABLE 8

| Sample | B | B' | B" |
|---|---|---|---|
| O.D. (-Bl) | 0.081 | 0.038 | 0.020 |

EXAMPLE 10

(Uric acid)

A color producing reagent solution is prepared by dissolving in 0.1M tris buffer solution (pH 7.1) 20 mg/dl of $NO_2$-TB, 0.1% by weight of phenol, 600 U/dl of peroxidase (available from Biozyme Co.), 10 mg/dl of glutathione (reduced form), and 30 U/dl of uricase (available from Toyobo Co., Ltd.)

Sample A is distilled water as blank, Sample B is a solution containing 10 mg/dl of uric acid obtained by dissolving 10 mg of uric acid in 100 ml of a 1% aqueous solution of lithium carbonate, and Sample C is high uric acid content serum containing 12 mg/dl of uric acid, said value being obtained by a conventional measuring method.

Each 3 ml of the color producing reagent solution is placed in 3 test tubes and each 60 μl of Samples A, B and C is added to each test tube, followed by incubation at 37° C. for 10 minutes. Immediately, absorbances of Samples B and C are measured at wavelength of 560 nm using Sample A as control. From the results shown in Table 9, the content of uric acid in Sample C is calculated as 21.8 mg/dl.

TABLE 9

| Sample | B | C |
|---|---|---|
| Absorbance | 0.074 | 0.088 |

EXAMPLE 11

(L-Lactic acid)

A color producing reagent solution is prepared by dissolving in 0.1M tris buffer solution (pH 7.5) 20 mg/dl of $NO_2$-TB, 0.1% by weight of phenol, 600 U/dl of peroxidase (available from Biozyme Co.), 10 mg/dl of glutathione (reduced form), and 85 U/dl of L-lactate oxidase.

Sample A is distilled water as blank, and Sample B is an aqueous solution containing 10 mM of sodium L-lactate and making the volume 100 ml.

Each 3 ml of the color producing reagent solution is placed in two test tubes and each 60 μl of Samples A and B is added to each test tube, followed by incubation at 37° C. for 10 minutes. Immediately, absorbance of Sample B is measured at wavelength of 560 nm using Sample A as control to give the value of 0.110.

EXAMPLE 12

(Cholesterol)

A first color producing reagent solution is prepared by dissolving in 0.1M tris buffer solution (pH 8.0) $3 \times 10^{-5}$ mole of oxidizing type cytochrome C (available from Sigma Chemical Co., type III), 0.1% by weight of phenol, 600 U/dl of peroxidase (available from Biozyme Co.), and 15 U/dl of cholesterol oxidase (available from Amano Pharmaceutical Co., Ltd.). A second color producing reagent solution is prepared by dissolving in 0.1M tris buffer solution (pH 8.0) 800 mg/dl of glutathione (reduced form).

Sample A is isopropanol as blank, Sample B is an isopropanol solution containing 200 mg/dl of cholesterol, and Sample C is blood serum containing 230 mg/dl of cholesterol, said value being obtained by a conventional measuring method. Further, Sample C is diluted with isopropanol 2 and 4 times to give Samples C' and C", respectively.

The first and second color producing reagent solutions are incubated at 37° C. Immediately before the measurement, to 4 ml of the first color producing reagent solution, 100 μl of the second color producing reagent solution and 20 μl of a sample are added and incubated at 37° C. for exactly 2 minutes. Subsequently, absorbances at wavelength of 550 nm are measured. The results are shown in Table 10.

TABLE 10

| Sample | A | B | C | C' | C" |
|---|---|---|---|---|---|
| $O.D._{550}$ | 0.210 | 0.316 | 0.336 | 0.274 | 0.240 |
| O.D. (-Bl) | — | 0.106 | 0.126 | 0.064 | 0.030 |

From the above results, the content of cholesterol in Sample C is 238 mg/dl. The values of Samples C, C' and C" show linearity.

What is claimed is:

1. A process for quantitatively determining a substrate, which comprises treating a sample containing a substrate selected from the group consisting of glucose, glycerol, glycerol phosphate, choline, cholesterol, acyl CoA, pyruvic acid, uric acid, xanthine and lactic acid with a specific oxidase corresponding to said substrate, and measuring the generated superoxide ion by using a reagent composition comprising (a) the specific oxidase, (b) a peroxidase, (c) a phenol and/or an amine, (d) a thiol compound in an amount effective to retard the conversion of superoxide into hydrogen peroxide, and (e) a color producing reagent to be reduced.

2. A process according to claim 1, wherein the measuring of the generated superoxide ion is conducted by applying reducing properties of superoxide ion.

3. A process according to claim 1, wherein the measuring of the generated superoxide ion is conducted by measuring color formation or color change produced by reduction of a color producing reagent to be reduced by the superoxide ion.

4. A process for quantitatively determining a substrate, which comprises treating a sample containing a substrate selected from the group consisting of glucose, glycerol, glycerol phosphate, choline, cholesterol, acyl CoA, pyruvic acid, uric acid, xanthine and lactic acid with a specific oxidase corresponding to said substrate, and measuring the generated superoxide ion, said oxidase treatment and measuring of generated superoxide ion conducted by measuring color formation or color change being conducted by using a reagent composition comprising (a) the specific oxidase, (d) a peroxidase, (c) a phenol, (d) a thiol compound in an amount effective to retard the conversion of superoxide into hydrogen peroxide, and (e) a color producing reagent to be reduced.

5. A proces for quantitatively determining a substrate, which comprises treating a sample containing a substrate selected from the group consisting of glucose, cholestrol, glycerol, glycerol phosphate, choline, acyl CoA, pyruvic acid, uric acid, xanthine and lactic acid with a specific oxidase corresponding to said substrate, and measuring the generated superoxide ion, said oxidase treatment and measuring of generated superoxide ion conducted by measuring color formation or color change being conducted by using a reagent composition comprising (a) the specific oxidase, (b) a peroxidase, (c) an amine, (d) a thiol compound in an amount effective to retard the conversion of superoxide into hydrogen peroxide, and (e) a color producing reagent to be reduced.

6. A process for quantitatively determining a substrate, which comprises treating a sample containing a substrate selected from the group consisting of glucose, cholesterol, glycerol, glycerol phosphate, choline, acyl CoA, pyruvic acid, uric acid, xanthine and lactic acid with a specific oxidase corresponding to said substrate, and measuring the generated superoxide ion, said oxidase treatment and measuring of generated superoxide ion conducted by measuring color formation or color change being conducted by using a reagent composition comprising(a) the specific oxidase, (b) a peroxidase, (c) a phenol and/or an amine, (d) a thiol compound in an amount effective to retard the conversion of superoxide intohydrogen peroxide, (e) a color producing reagent to be reduced, and (f) a chelating reagent.

7. A composition for quantitative determination of a substrate comprising in a mixture (a) a specific oxidase corresponding to a substrate to be determined, (b) a peroxidase, (c) a phenol, (d) thiol compound in an amount effective to retard the conversion of superoxide into hydrogen peroxide, and (e) a color producing reagent to be reduced, said substrate being selected from the group consisting of glucose, glycerol, glycerol phosphate, choline, cholesterol, acyl CoA, pyruvic acid, uric acid, xanthine and lactic acid, the components of the mixture being present in amounts effective for quantitatively determining a substrate.

8. A composition for quantitative determination of a substrate comprising in a mixture (a) a specific oxidase corresponding to a substrate to be determined, (b) a peroxidase, (c) an amine, (d) a thiol compound in an amount effective to retard the conversion of superoxide into hydrogen peroxide, and (e) a color producing reagent to be reduced, said substrate being selected from the group consisting of glucose, cholesterol, glycerol, glycerol phosphate, choline, acyl CoA, pyruvic acid, uric acid, xanthine and lactic acid, the components of the mixture being present in amounts effective for quantitatively determining a substrate.

9. A composition for quantitative determination of a substrate comprising in a mixture (a) a specific oxidase corresponding to a substrate to be determined, (b) a peroxidase, (c) a phenol and/or an amine, (d) a thiol compound in an amount effective to retard the conversion of superoxide into hydrogen peroxide, and (e) a color producing reagent to be reduced and (f) a chelating agent, said substrate being selected from the group consisting of glucose, cholesterol, glycerol, gylcerol phosphate, choline, acyl CoA, pyruvic acid, uric acid, xanthine and lactic, acid the components of the mixture being present in amounts effective for quantitatively determining a substrate.

* * * * *

UNITED STATES PATENT AND TRADEMARK OFFICE
CERTIFICATE OF CORRECTION

PATENT NO. : 4,695,539

DATED : September 22, 1987

INVENTOR(S) : SAKATA et al

It is certified that error appears in the above-identified patent and that said Letters Patent is hereby corrected as shown below:

On the cover page, Item [75], line 1, "Yoshibonu" should read --Yoshinobu--.

Signed and Sealed this

Twenty-first Day of June, 1988

*Attest:*

DONALD J. QUIGG

*Attesting Officer*     *Commissioner of Patents and Trademarks*